United States Patent [19]

Sjöstrand

[11] 4,188,943
[45] Feb. 19, 1980

[54] METHOD OF PRODUCING A DISMOUNTABLE, REINFORCED PLASTER MOLD OR PLASTER CAST AND MEANS THEREFOR

[76] Inventor: Gunnar Sjöstrand, Box 268 A, Åtvidaberg, Sweden, S-597 00

[21] Appl. No.: 835,028

[22] Filed: Sep. 20, 1977

[30] Foreign Application Priority Data

Sep. 23, 1976 [SE] Sweden .............................. 7610530

[51] Int. Cl.² ............................................. A61F 5/04
[52] U.S. Cl. .................................. 128/91 A; 128/91 R
[58] Field of Search ............... 128/83, 83.5, 90, 91 A, 128/91 R; 35/20; 32/17; 249/155; 425/2

[56] References Cited

U.S. PATENT DOCUMENTS

| 221,569 | 11/1879 | Johnson | 425/2 |
| 539,617 | 2/1895 | Harrington | 249/155 |
| 542,390 | 7/1895 | Linn | 128/82 |
| 2,230,781 | 2/1941 | Longfellow | 128/91 A |
| 3,085,569 | 4/1963 | Cook et al. | 128/91 R |
| 4,041,941 | 8/1977 | Driver | 128/91 A |

FOREIGN PATENT DOCUMENTS

943586 12/1963 United Kingdom ...................... 425/2

OTHER PUBLICATIONS

*The Journal of Bone and Joint Surgery*, vol. 23, No. 1, Jan. 1941, p. 184, Wilson, "A Simple Method of Applying Plaster Casts to Provide for Easy Removal".

*Primary Examiner*—Robert W. Michell
*Assistant Examiner*—Thomas Wallen
*Attorney, Agent, or Firm*—Cushman, Darby & Cushman

[57] ABSTRACT

A method of producing a dismountable web reinforced plaster cast for supporting an interior mold, comprising covering the mold with an elastic stocking, covering said stocking with a rubber layer in the form of thin latex rubber strips, treated with talcum, by winding said strips around said stocking, placing at least two longitudinally extending border lists each with an inserted wire along the highest contours of the mold by means of self-adhesive tape which adheres to the underlying rubber winding applying plaster reinforced with fabric around said rubber winding and said border lists, allowing the plaster to solidify, cutting the plaster along chords at the lists using said wires as guides for the cutting tool so that the latter does not cut too deeply into the plaster, removing the resulting plaster segments, separating the remaining parts of plaster from the mold, drying said parts in an oven so that the excess water is removed, restoring said parts with intermediate border lists around the mold, and fixing said parts relative to each other by winding with a bandage.

6 Claims, 8 Drawing Figures

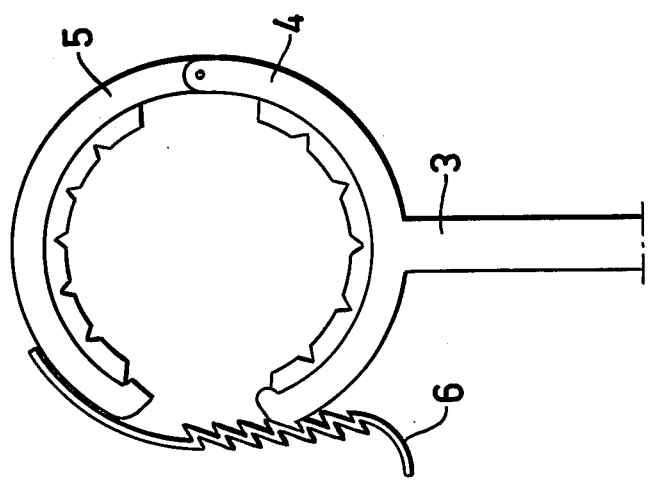
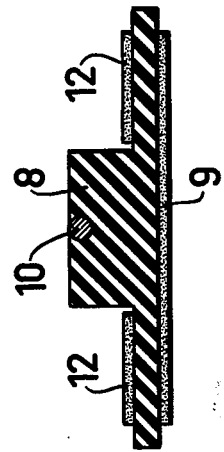
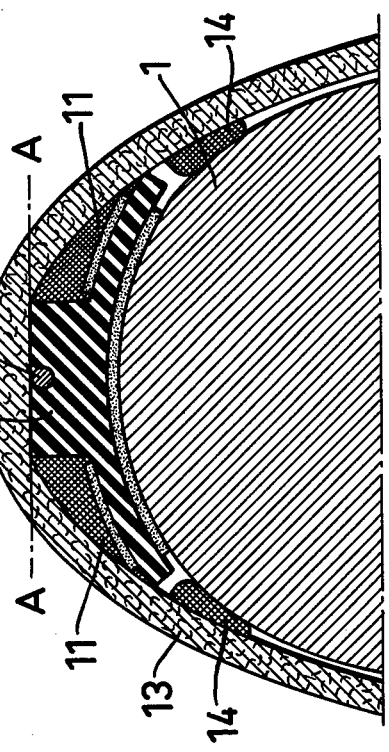

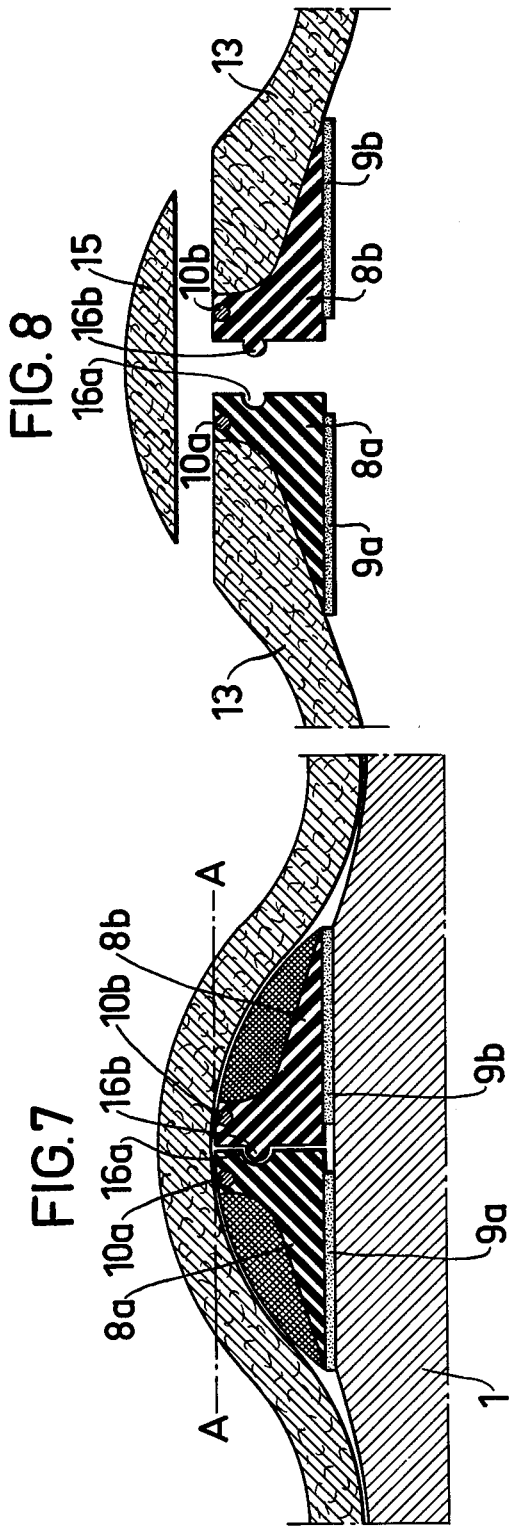
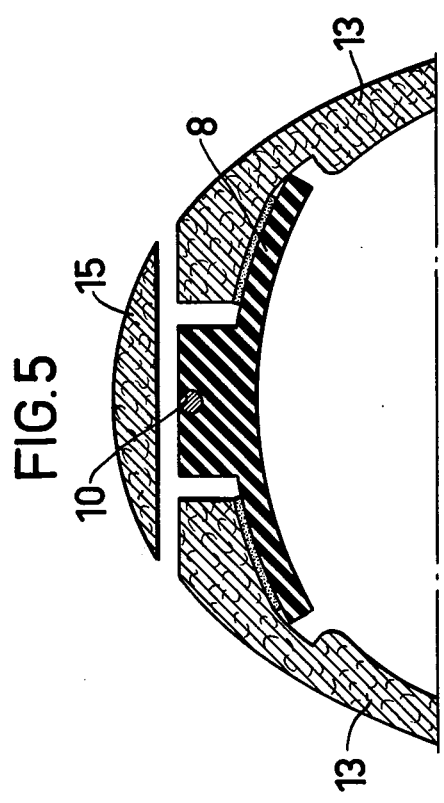
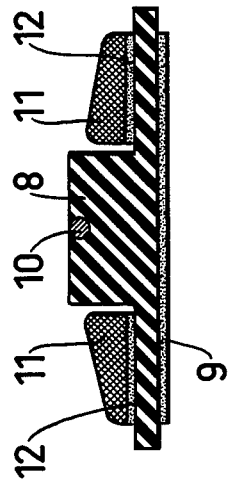

METHOD OF PRODUCING A DISMOUNTABLE, REINFORCED PLASTER MOLD OR PLASTER CAST AND MEANS THEREFOR

Plaster molds are used for several purposes, from the plaster casts of footmarks in detective branch technics to the plaster bandages used when dressing broken limbs. When stuffing animals plaster casts of the dead animal are often used to get a correct reproduction of muscles and the like.

This invention relates more specifically to a method of producing an essentially improved plaster mold or plaster cast with great advantages within several application fields.

Divisible plaster molds have been used for a long time when producing casts of objects of art, such as statues and the like. However, in spite of all technical development in the last decades primitive methods are still used requiring a great skill. The same applies to plaster cast bandages and dressings around injured or broken limbs of animals and human beings, where methods used also require a skill developed by practice in order to obtain a good result.

In veterinary surgery, where you are often forced to secure a broken leg or the like by splints, a plaster cast bandage is still being used, which involves great disadvantages, among other things due to the long drying time required. Certainly the plaster solidifies rapidly, but the excess of water is to evaporate and, meanwhile, the bandage is relatively weak and, above all, has a soft surface. When such a bandage is then to be removed, it is found, as a rule, that the bandage sticks to underlying hair tegument or the like making it necessary to anaesthetize the injured animal at removal, and that the following irritation or smarting pain are extremely annoying even if infections do not supervene. The same applies to a large extent also to a corresponding supporting dressing around human limbs or the like.

Moreover, these traditional plaster bandages, whether human beings or animals are concerned, must often be broken up, for swelling or off-swelling of the treated part of the body may require a new bandage. An X-ray control also requires breaking up, as it is not desired to expose the patient to the strong X-ray doses necessary to penetrate the bandage.

Thus, the problem that this invention is intended to solve, is to achieve an exactly fitting, armoured or reinforced plaster cast bandage of a very good strength which does not stick to the substrate, especially if this is hairy, it being necessary, moreover, that the plaster is finished, i.e. dry in a minimum of time and the mold, furthermore, should have such properties that it is easy to remove it for inspection of the mold core and then easy to put it together with or without mold core. In addition, it should preferably be adjustable within certain tolerances so that it can be adapted handily to a swelling or off-swelling. No such plaster mold coveted both by veterinaries and doctors, and useful also for curators and other people working with plaster casts has previously been found. There has been no lack of attempts, for especially the problem with the removal of the plaster without damaging the cast object or injuring the patient has been urging. Thus, in the U.S. Pat. No. 2,206,339 teaches a supporting dressing of circularly wound plaster provided with a guide groove for a cutting means in the form of an inert consisting of an elastic material, which is to be placed on a part of the body and surrounded by plaster. According to the specification the guide means serve to make breaking up of the plaster mold easier after cutting. In another U.S. Pat. No. 2,230,781 the introduction of a harder material in a groove in the mold as a protection against unintentional cuts is suggested. Then a wire or the like is introduced in a groove in the bandage to prevent the cutting means from comimg down to the extremity. In both cases means to facilitate breaking off the plaster cast bandage are concerned, which is often the cause of injuries to the patient and, in any case, mostly painful.

In order to prevent hairy tegument or the like to stick to the plaster various kinds of stockings have been suggested, but, as a rule, these have been encumbered with drawbacks of one kind or other.

In the veterinary field this has led to plastering failures and to complication of the healing of broken limbs. Also in hospital treatment it has been found that the circular bandages used often give rise to erroneous healing and the like, which requires breaking up and new plastering. Very expensive time both for the doctor and the patient is wasted as a consequence of the disadvantages in the above respect of the plaster bandages used so far. The method of the invention is built on several coactive factors. The first one, viz, to find a suitable isolation of a haired surface which does not compress or deform the mold, has after long series of tests been found to be so-called dentist rubber, sold under the name of "Kofferdam". This is thin and has a width of about 4 cm and is carefully wound around the extremity possibly covered with a stocking under such a stress that the strip follows the lines of the wound mold without causing any deformation itself. An absolutely sealing surface coating is then obtained, which neither irritates the underlying skin or causes any stagnation of the blood. This rubber material contains on its surface much talc and will therefore release the applied plaster surface without any adhesion whatsoever. However, it cannot be used twice with advantage.

The discovery of this material was combined with experiments with a suitable joining means to make possible the division of the plaster mold into various sections. According to the invention border lists made from a soft rubber compound with a hardness lying between 40 and 60 Shore, particularly around 55 Shore, and with at least one rail or wire of soft iron disposed in the outer limiting surface of the outer profile and which forms the outer profile of the border list, are adapted on the highest surfaces of the model, carcass or extremity relative to an imaginary geometrical center. It is important that this rail or wire projects above the surface of the rubber compound in order not to make later cutting difficult. If the rail or the wire is covered by a rubber film somewhere, the cutting means will easily stick to this. Furthermore, the border list is provided with a double-sided tape whose underside makes it easy to attach the border list to the underlying rubber winding. The tested hardness of the rubber list and the soft iron wire provided in combination an absolutely dumb workability, thanks to which the edge list can be made to follow the substrate without rebound and stresses.

If the case part of the body has marked hollows, suitable pads of e.g. plaster impregnated fabric are possibly inserted, after which the mold is formed by means of circular plastering in the usual way. The number or necessary turns can be reduced in cmparison with what has so far been considered as necessary in circular plastering.

The plaster mold thus produced is allowed to solidify for a few minutes, the burnt plaster absorbing water of crystallization solidifying. However, the major portion of the water of the plaster compound still remains in the mold. So far this has evaporated in the course of several days before the mold obtains its full strength and meanwhile it causes irritation and inconvenience for a possible patient. This has especially complicated the use of a plaster case bandage at a fracture of a domestic animal and the like having difficulties in patiently tolerating maltreatment in the form of a constantly irritating formentation.

As soon as the plaster has solidified the mold is preferably, according to the invention, cut open with a band knife along chords at the border lists so as to remove segments of the plaster, the annealed iron wire serving as a guide for the band knife. It is very easy to cut the still wet plaster. The mold now in two halves or several parts is carefully removed and placed in a suitable drying box (oven), where the parts of the mold are left to dry for 15–20 min at a suitable temperature and ventilation, after which the considerably lighter and much stronger mold parts are taken out and placed together again, without a core if a cast is concerned, or around the injured extremity or the like in the event of a supporting dressing. In the latter case the mold body is conveniently fixed in a definite position of an adjustable support means designed for this purpose. Before the mold parts are adapted the rubber strip is preferably unwound, which has now served its purpose, and the mold parts are adapted with inserted border lists. The fit can be adjusted afterwards because the border lists are made in such a way that they permit release from the plaster and, if desired, they can be exchanged for somewhat narrower or broader lists which are placed in the mold by means of their uppertape surface before the final assembly of the mold. The mold parts are thereafter fixed with externally arranged, wound bandages of a suitable material e.g. self-adhesive plastic tape.

The plaster mold obtained in this way is a considerable improvement from all points of view in comparison with that of older methods, and in clinical use it has given greatly improved healing results both for animals and human beings.

Above all this applies to plastering of fractured legs of dogs, which surprisingly well tolerate bandages of this type, probably on account of the fact that the feeling of irritation from the formentation which has earlier been inevitable is eliminated and consequently also the irritation previously resulting in that the bandage has been gnawn to pieces or crushed at the first opportunity. By means of the plaster cast bandage of the invention the patient, whether an animal or a human being is concerned, is spared the painful long-term drying of the bandage, and, moreover, this can be opened without too great troubles for inspection, treatment of wound injuries and skin irritations and for possible X-raying. At dressing the lists can be exchanged to compensate for a swelling or an off-swelling. The breaking up procedure so far very painful for the patient, which has required anaesthetizing at e.g. dogs, is completely eliminated.

If the mold is intended for casting in connection with so-called stuffing, a detailed and exact mold is quickly obtained, whose size can be easily adjusted by means of narrower (or broader) border lists, which is often desirable to compensate for skin, feathers or the like, which are to be applied later on to a cast.

The essential embodiment of a plaster mold or a plaster bandage according to the invention will appear from the above, but for the sake of clearness an embodiment will be described below more in detail in connection with the enclosed drawings, wherein FIG. 1 shows a front leg of a dog in a schematic fixture as seen from above, FIG. 2 shows a detail of the fixture in FIG. 1, FIG. 3 shows a section of a simple embodiment of the border list according to the invention, FIG. 4 shows the same list in use seen in section with core and surrounding plaster cast bandage, FIG. 5 shows the same element as in FIG. 4 but with the various parts of the mold being loosened.

FIG. 6 shows a section of the same list as in FIG. 3 provided with self-adhesive tape on the upper side as well as the underside with taped intermediate pads.

FIG. 7 shows a section of a list used as partition list at a relatively plane position of the mold and FIG. 8 shows the same list after the parts being moved apart.

Figure 1:
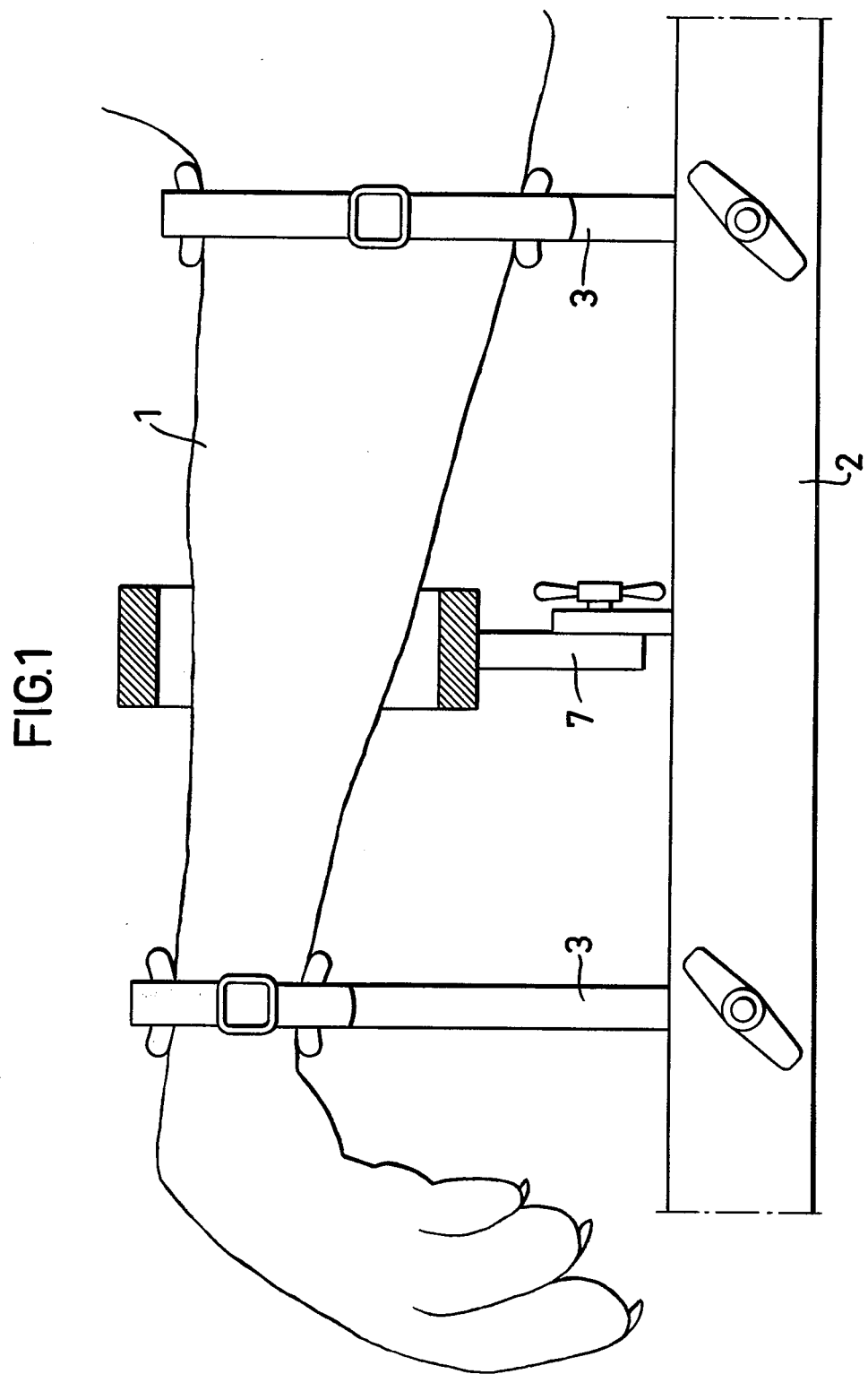

The method of applying a supporting dressing according to the invention is apparent from what has been stated above. However, as is made clear in FIG. 1, an injured part of the body, in this case a front leg 1 of a dog can be adapted on or in a fixture after carefully winding the leg with an envelop of the above-mentioned "dentist rubber". The fixture can be designed in an arbitrary manner but preferably contains a supporting frame 2, which can be formed as a part of a reclining shelf or a seat board and which can be fixed in a definite position relative to the shelf or board. The frame 2 preferably carries a number of adjustable and fixable supports 3, whose supporting parts can be designed as articulated securing means, as is shown in FIG. 2. In this case these means consist of a lower fork-shaped part 4, which can be suitably adjusted vertically and which coacts with an upper clamp 5, preferably provided with a resilient toothed means 6, which coacts with a corresponding tooth (or teeth) in the lower fork 4. In this way the clamp 4, 5 preferably covered with rubber can be gradually closed, and it can be opened in a moment by loosening the resilient member 6 of the part 5 outwards. In many cases it can be suitable with an extra support designated by 7 in FIG. 1, which can be designed in a suitable way.

A plaster cast bandage according to the invention can of course be formed without such a means, but a fixture has been found to be practical in many cases, above all in taxidermist technique and in work with anaesthetized animals or the like.

After fixing the injured extremity or the like in a right position and optionally providing it with a stocking, it is thus tied with rubber strips of aforesaid type to prevent coat and skin from sticking to the plaster cast bandage. It is also the object of this rubber strip to coact according to the invention with the adhesive tape on the border lists.

An embodiment of such a border list 8 is apparent from FIG. 3. It consists of a string provided with flanges, which is made from a rubber compound of a hardness of between 40 and 60 Shores. The flanges on the sides give a satisfactory contact surface against the wound rubber strip. A double-adhesive textile tape 9, which is adapted on the underside of the list, makes possible a fixation to a substrate. The very moderate resilience of the rubber list is counteracted by an annealed wire of soft iron 10 and this soft annealed iron wire 10 has a suitable plasticity and, moreover, a hardness, which is enough to be able to control a cutting knife not shown, usually a band knife. In addition, in FIG. 6 two inserts 11 are shown in the form of plaster prepared strips made from coarse fabric, wires or the like, and these are retained to the list with the aid of self-adhesive tapes on the upper side of the flanges of the border list 8, see FIG. 6.

In FIG. 4 a schematic section of part of a circular plastering is shown where the list 8 has been adapted along an outer profile of the mold, the leg 1. The plaster bandage is marked by 13 and combines in solidification with the prepared inserts 11 and with possibly inserted extra cavity filling strips marked with 14. When the bandage after solidification is cut along chord the line A—A, the wire 10 serving as guide, an edge segment 15 is released, and the various elements will enter the position schematically shown in FIG. 5. As a consequence of the moisture of the plaster at this stage the border lists 8 will at once release the plaster envelop 13, which is then placed in an oven or a heating chamber for drying.

At the assembly of the mold following upon drying either the same list as before can be used or else a broader or thinner one. Depending on the field of use the self-adhesive tape 9 can e.g. be removed; in certain cases, e.g. at a supporting dressing, it can be practical to let the list 8 remain in a portion of the mold during the drying procedure.

The plaster halves or parts 13 will have the profile in solidification, which is apparent from FIG. 5, and with strong edges towards the list 8.

In FIG. 7 a schematic section of a bandage with a two-piece list according to the invention is shown. This list is longitudinally divided into strips 8a and 8b respectively, which are provided with two self-adhesive tapes 9a, 9b on their undersides. The list portion 8a is provided with a longitudinal groove 16a and the part 8b with a corresponding projecting list 16b. The groove and the list form together a sealing joint, which can be pressed together to the position in the figure. At the embodiment shown the two list portions are provided with each their cast wire 10a and 10b of soft iron to control the cutting means, when the mold is to be divided. The appearance of the mold parts is evident from FIG. 8.

The embodiment of the list profile as well as its dimensions can of course be varied to a large extent within the scope of the following claims. Various fixtures can for instance also be arranged to simplify the adaptation of the lists in their right position and the mold core can of course be covered with coatings of different kinds to secure that the self-adhesive surfaces of the lists adhere and, respectively, that the plaster bandage comes off.

It can be pointed out that if a joint follows a sharp edge it is suitable to use a two-pice list designed so that the flanges at 8a and 8b form an obtuse angle with each other. In certain cases it can be suitable at the repeated assembly of the mold also to restore the cut off part 15 in order that the tape or the like wound around should tend to draw the mold parts obliquely relative to each other.

What I claim is:

1. A method of producing a removable plaster cast for a body comprising: applying to the body at least two soft, rubber-like border lists in the form of strips which extend longitudinally of the body, each of the border lists including a rail or wire of harder material extending along the length of the list and being exposed at the outer surface thereof; surrounding the body and lists with wet plaster reinforced with filamentary material; allowing the plaster to harden; removing a segment of plaster from the outer surface of each list by cutting along a chord which lies tangent to the wire, while using the wire as a guide for the cutting tool, thereby exposing the outer surfaces of the lists; and separating the remaining plaster parts from the lists and from the body.

2. A border list for carrying out the method of claim 1 having a hardness of between 40 and 60 Shore carrying at least one longitudinal rail or wire of a harder material arranged in the outer limiting surface of the outer profile over which the plaster bandage or the like is wound, the wire or the rail being intended to form a guide for the cutting means.

3. The list as claimed in claim 2, characterized in that it is provided with a double-adhesive textile tape or the like on the underside, the tape binding the list to the mold.

4. The list as claimed in claim 2, characterized in that it is provided with two flanges both provided with double-adhesive tape on the upper side to retain inserts of plaster fabric or the like intended to level cavities in the range around the list following the profile.

5. The list as claimed in claim 2, characterized in that it is longitudinally divided into two halves, which are kept together by e.g. groove and tenon elements, by means of which the two parts of the list can be joined and loosened from each other respectively.

6. A method of producing a dismountable web reinforced plaster cast for supporting an interior mold, comprising covering the mold with an elastic stocking, covering said stocking with a rubber layer in the form of thin latex rubber strips, treated with talcum, by winding said strips around said stocking, placing at least two longitudinally extending border lists each with an inserted wire along the highest contours of the mold by means of self-adhesive tape which adheres to the underlying rubber winding, applying plaster reinforced with fabric around said rubber winding and said border lists, allowing the plaster to solidify, cutting the plaster along chords at the lists using said wires as guides for the cutting tool so that the latter does not cut too deeply into the plaster, removing the resulting plaster segments, separating the remaining parts of plaster from the mold, drying said parts in an oven so that the excess water is removed, restoring said parts with intermediate border lists around the mold, and fixing said parts relative to each other by winding with a bandage.

* * * * *